United States Patent
Sato et al.

(10) Patent No.: US 9,532,521 B1
(45) Date of Patent: Jan. 3, 2017

(54) DWARF LUPINE

(71) Applicant: Green Fuse Botanicals, Inc., Santa Monica, CA (US)

(72) Inventors: Kazunori Sato, Tokyo (JP); Tsutomu Semba, Mooka (JP)

(73) Assignee: Green Fuse Botanicals, Inc., Santa Monica, CA (US)

( * ) Notice: Subject to any disclaimer, the term of this patent is extended or adjusted under 35 U.S.C. 154(b) by 0 days.

(21) Appl. No.: 14/954,952

(22) Filed: Nov. 30, 2015

(51) Int. Cl.
*A01H 5/02* (2006.01)
*A01H 1/02* (2006.01)

(52) U.S. Cl.
CPC . *A01H 5/02* (2013.01); *A01H 1/02* (2013.01)

(58) Field of Classification Search
None
See application file for complete search history.

(56) References Cited

U.S. PATENT DOCUMENTS

PP18,802 P2 * 5/2008 Conibear ................. A01H 5/02

OTHER PUBLICATIONS

Clements et al 2008, 'Lupins for Health and Wealth' Proceeding of the 12th International Lupin Conference, Sep. 13-18, 2008, Fremantle, Western Australia. International Lupin Association, Canterbury, New Zealand. pp. 324-327.*
Sator 1990, Chapter III.3 Lupins (*lupinus* spp.) in Biotechnology in Agriculture and Forestry, vol. 10 Legumes and Oilseed Crops 1, Y.P.S. Bajaj editor, Springer-Verlag Berlin Heidelberg.*
Harzic et al 1996, Agronomie 16: 309-319.*
Griffiths 1994, in Index of Garden Plants, Timber Press, Portland, Oregon, pp. 697-698.*
Newton et al 2010 Institute for Applied Ecology, Corvallis, Oregon and USDI Bureau of Land Management, Vale District, iii + 7pp.*
Watanabe et al 1993 Chem. Pharm. Bull. 41(2): 394-396.*

* cited by examiner

*Primary Examiner* — David H Kruse
(74) *Attorney, Agent, or Firm* — Barbara Campbell; Cochran Freund & Young LLC

(57) ABSTRACT

Lupine plants comprising a homozygous recessive mutant allele that produces a dwarf plant height characteristic (or dwarf plant height phenotype or trait) are disclosed. One embodiment relates to the seeds of said dwarf lupine plants, to the plants of said dwarf lupine plants, to plant parts of said dwarf lupine plants, and to methods for producing a lupine plant produced by crossing said dwarf lupine plant with itself or with another lupine plant. Another embodiment also relates to methods for producing a lupine plant having a dwarf plant height characteristic (or dwarf plant height phenotype or trait) and to the dwarf plant height characteristic (or dwarf plant height phenotype or trait) lupine plants and plant parts produced by those methods. Another embodiment relates to producing interspecific lupine dwarf plants having a dwarf plant height characteristic (or dwarf plant height phenotype or trait).

20 Claims, 9 Drawing Sheets

DWARF LUPINE

BACKGROUND

All publications cited in this application are herein incorporated by reference. *Lupinus*, commonly known as lupin or lupine, is a genus of flowering plants in the legume family, Fabaceae. The genus includes over 200 species, including *polyphyllus, arboreus, sulphureus*, and *nootkatensis*. *Lupinus polyphyllus* (also known as large-leaved lupine, or, primarily in cultivation, garden lupine) is a species of lupine (lupin) native to western North America from southern Alaska and British Columbia east to Alberta and western Wyoming, and south to Utah and California and commonly grows along streams and creeks, preferring moist habitats.

Lupine can be propagated from seed, cuttings, and tissue culture. Seed, cuttings and tissue culture germination protocols for Lupine are well-known in the art.

Lupine is an important and valuable ornamental plant. Thus, a continuing goal of ornamental plant breeders is to develop plants with novel characteristics, such as color, growth habit, and hardiness. To accomplish this goal, the breeder must select and develop plants that have traits that result in superior Lupine varieties.

The foregoing examples of the related art and limitations related therewith are intended to be illustrative and not exclusive. Other limitations of the related art will become apparent to those of skill in the art upon a reading of the specification.

SUMMARY

Figure 1:
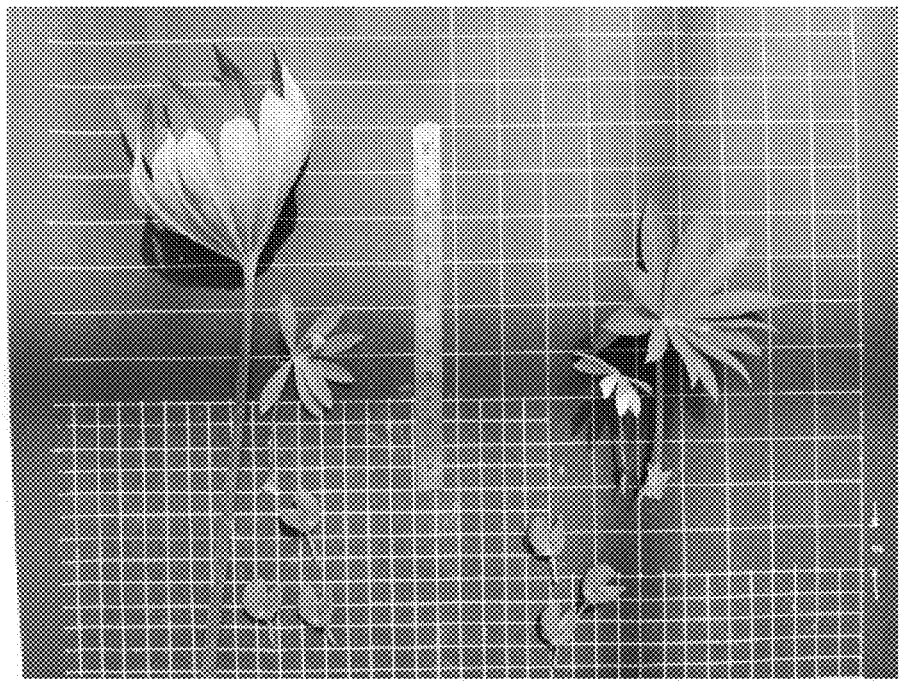
FIG. 1 is a photo comparing the immature leaves, leaflets, petioles, and individual florets between a tall Russell Reliance series red plant on the left with a dwarf red plant on the right. The plants are approximately 7 months old from seed.

The following embodiments and aspects thereof are described in conjunction with systems, tools and methods which are meant to be exemplary, not limiting in scope. In various embodiments, one or more of the above-described problems have been reduced or eliminated, while other embodiments are directed to other improvements.

According to one embodiment, there is provided a lupine plant comprising a homozygous recessive mutant allele that produces a dwarf plant height characteristic (or dwarf plant height phenotype or trait. Plants of said lupine are further valued as breeding lines enabling the development of superior ornamental lupine plants having a dwarf plant height and a range of desirable flower color and superior growth performance.

Another embodiment discloses a lupine plant comprising a homozygous recessive mutant allele that produces a dwarf plant height characteristic, wherein said dwarf plant characteristic comprises a lupine plant having a plant height with raceme of less than 35.0 cm, wherein a sample of representative seed of said lupine plant comprising said homozygous recessive mutant allele that produces a dwarf plant height is deposited under NCIMB No. 42442.

Another embodiment discloses a lupine plant comprising a homozygous recessive mutant allele that produces a dwarf plant height characteristic, wherein said dwarf plant characteristic comprises a lupine plant having a dwarf plant height without raceme of less than 13.0 cm, wherein a sample of representative seed of the lupine plant comprising a homozygous recessive mutant allele that produces a dwarf plant height is deposited under NCIMB No. 42442.

Another embodiment relates to tissue culture produced from protoplasts or cells from the Lupine plants disclosed in the subject application, wherein said cells or protoplasts are produced from a plant part selected from the group consisting of pollen, ovules, embryos, protoplasts, meristematic cells, callus, pollen, leaves, ovules, anthers, cotyledons, hypocotyl, pistils, roots, root tips, flowers, seeds, petiole, pods, and stems.

In addition to the exemplary aspects and embodiments described above, further aspects and embodiments will become apparent by study of the following descriptions.

DEFINITIONS

In the description and tables herein, a number of terms are used. In order to provide a clear and consistent understanding of the specification and claims, including the scope to be given such terms, the following definitions are provided:

Allele. Allele is any of one or more alternative forms for a gene.

Dwarf. As used herein, "dwarf" refers to a lupine plant that is phenotypically shorter in plant height when compared with a commercial lupine plant of the same type and age, and is homozygous recessive for the mutant allele disclosed in this application for plant height.

Raceme. As used herein, a "raceme" refers to the flowers and that portion of the peduncle containing the flowers of the plant.

Gene. As used herein, "gene" refers to a segment of nucleic acid.

Locus. A locus is the position or location of a gene on a chromosome.

Plant Diameter. Plant diameter is the spread of the plant, as measured at the widest horizontal part of the plant.

Plant Form. Plant form refers to the silhouette or profile of the plant, ranging from upright to semi-spreading to spreading.

Plant Height Without Raceme. Plant height without raceme is the plant height measured from the top of the soil to the top of the foliage.

Plant Height With Raceme. Plant height with raceme is the plant height measured from the top of the soil to the top of the flowering raceme.

Progeny. As used herein, the descendants of one or more of the parental lines and includes an $F_1$ lupine plant produced from the cross of two lupine plants where at least one plant includes a lupine plant disclosed herein and progeny further includes, but is not limited to, subsequent $F_2$, $F_3$, $F_4$, $F_5$, $F_6$, $F_7$, $F_8$, $F_9$, and $F_{10}$ generational crosses with the recurrent parental line.

RHS. RHS refers to the acronym for Royal Horticultural Society that publishes a color chart used in the plant industry. All RHS colors referred to herein are from the RHS 2007 edition.

Single Gene Converted (Conversion). Single gene converted (conversion) plants refers to plants which are developed by a plant breeding technique called backcrossing wherein essentially all of the desired morphological and physiological characteristics of a variety are recovered via the backcrossing technique in addition to the single gene transferred into the variety via the initial cross or via genetic engineering.

DETAILED DESCRIPTION

There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possesses the traits to meet the program goals. The goal is to combine improved combination of desirable traits from the parental germplasm. These important traits may include flower color, certain plant characteristics, higher vigor, resistance to diseases and insects, better stems and roots, tolerance to drought and heat, and better commercial plant and flower quality.

The present application discloses lupine plants comprising a homozygous recessive mutant allele that produces a dwarf plant height characteristic (or dwarf plant height phenotype or trait), wherein said lupine plants have a dwarf plant height with a raceme of less than 35.0 cm, wherein a sample of representative seed of the lupine plant comprising a homozygous recessive mutant allele that produces a dwarf plant height is deposited under NCIMB No. 42442. Plants of said lupine are further valued as breeding lines enabling the development of superior ornamental lupine plants having a dwarf plant height and a range of desirable flower color and superior growth performance.

The novel lupine disclosed in the present application are unique in that they exhibit a dwarf plant height. Specifically, a plant height as measured to the top of the raceme, of 35.0 cm or less, while retaining the growth rate and form of commercial tall lupine varieties. The novel dwarf lupine disclosed in the present application are stable for a variety of colors and characteristics.

The present application also discloses a lupine plant comprising a homozygous recessive mutant allele that produces a dwarf plant height characteristic, wherein said dwarf plant characteristic comprises a lupine plant having a dwarf plant height without raceme of less than 13.0 cm, wherein a sample of representative seed of the lupine plant comprising a homozygous recessive mutant allele that produces a dwarf plant height is deposited under NCIMB No. 42442.

The dwarf lupine disclosed in the present application have shown uniformity and stability, as described in the following section. The dwarf lupine disclosed in the present application have been asexually and sexually reproduced a sufficient number of generations with careful attention to uniformity of plant type and has been increased with continued observation for uniformity.

Origin of Russell Hybrid Lupine

Commercial Russell hybrid lupine, *Lupinus polyphyllus* hybrid, were thought to be brought from North America to Britain in the 1820's. Russell hybrids, *Lupinus russellii hort*, were bred because *Lupinus polphyllus* originally were of basic colors, white pink to purple-blue flowers, and had large gaps in the flowering raceme. Please see United States Department of Agriculture, "Big Leaf Lupine", published October 2012. Over the decades, Russell hybrid plants were selected having denser racemes and more colors than the original *Lupinus polyphyllus*, but with the overall same plant height as a *Lupinus polyphyllus* plant.

To date, only tall or semi-tall Russell Lupine (*Lupinus polyphyllus* hybrid) are available in the commercial market. The average commercial Russell Lupine is about 4 feet tall. Thus, the lupine with a dwarf plant height disclosed in the present application are novel dwarf to extreme-dwarf lupine in that the plant heights, as measured from the top of the soil to the top of the raceme are less than 35.0 cm. Lupine plants having this dwarf characteristic, phenotype, or trait have short internodes and dense flowering racemes. The dwarf plant height characteristic, trait, or phenotype is heritable and enables creating new lupine for use in the front line of flower beds (due to its very short plant height), as dividers between different plant types, or in combination flower beds with commercial tall lupine varieties. The dwarf lupine disclosed in the present application exhibit a very short plant height without the use of any plant growth regulators. The commercial advantages of the novel dwarf lupine plants are an increased number of potted plants per shipping rack and a higher number of pots per square meter of growing area because of the smaller size of the plants, creating a competitive advantage in market by reducing the cost of production of the plants and the sales prices of the plants.

EXAMPLES

1. Development and Discovery of Lupine Plants Having a Dwarf Plant Height Characteristic The development of the dwarf Lupine disclosed in the present application resulted from a breeding program to develop Russell Lupine plants using the commercial series Minaret having an ideal plant type, such as straight flowering racemes, a wide assortment of flower colors, and uniform plants habits for each color. The original parental lupine plants were proprietary *Lupinus polyphyllus* hybrids. In March 2005 in Moka-shi, Tochigi, Japan, the inventors began hand-pollinating and selecting plants derived from the proprietary parental lupine lines. Seeds of 15 selected $F_1$ lines were collected, planted, and hand-pollinated. In 2006, 60 lines were selected from the $F_2$ and hand-pollinated. In 2007, 140 lines were selected from the $F_3$ and hand-pollinated. In 2009, 30 lines were selected for further development and breeding. Among the plant lines selected in 2009, in particular, the pink-white bi-color lines, an individual plant having a very short plant height was discovered and started flowering when the plant was only 10.0 cm in plant height. This individual plant had a favorable composition of flowering racemes, foliage, very compact plant habit, and very bushy plant habit.

Determination of Genetic Mechanism and Inheritance of Dwarf Lupine Plant Height Characteristic Plant height in lupine is determined by a gene, where the T, tall gene, is the dominant, and in commercially available tetraploid *Lupinus polyphyllus* hybrid lines for example, only the homozygous tall (i.e., TTTT) is known. Thus, the dwarf *L. polyphyllus* hybrid tetraploid lines disclosed in the present application must be homozygous for the recessive form of the gene, that is tat. To test this hypothesis, in 2009, the inventors crossed a dwarf Lupine plant disclosed in the present application with proprietary lines derived from an original commercial tall Lupine *Lupinus polyphyllus* hybrid variety. Seeds from the cross were planted and in March 2010, it was observed that all (100%) 150 individual plants were tall (and most likely heterozygous, TtTt). Twelve lines from the 150 plants were selected and hand-pollinated (self-pollinated). Approximately 800 seeds were obtained from each line and approximately 10,000 seeds ($F_2$) were planted in total. The $F_2$ was planted in October 2010 and 24 individual lines were recorded that exhibit the dwarf plant height characteristic, trait, or phenotype (very short plant height). That is, the inventor selected among the seedlings that exhibited the dwarf phenotype, the best 24 seedlings having the dwarf plant height phenotype out of the population to continue. The individuals were self-pollinated again and re-selected for the next generation. In March 2013, the $F_4$ was confirmed to be fixed and stable in color and plant height.

Through breeding and laboratory techniques well-known in the art, dwarf lupine plants can be produced as a homozygous tetraploid or diploid. Additionally, the dwarf plant height trait can be transferred stably and predictably across different lupine species, different colors, and different genetic backgrounds.

2. The Characteristics of Dwarf Lupine Plants Having the Dwarf Plant Height Characteristic Tables 1 to 4 show botanical characteristics between the dwarf lupine plants having the dwarf plant height characteristic, trait, or phenotype as compared to the tall Russell Reliance series varieties by each color. The dwarf lupine were sown on Oct. 15, 2014 into plug trays and transplanted into 10.5 cm pots on Nov. 6, 2014. The night-time temperatures were 5 degrees Celsius after transplanting until bloom time. No additional cold treatment for vernalization was given. The highest daytime temperatures were controlled below 10 degrees Celsius and no plant growth regulators were used. No artificial light was used and irrigation was done through the bottom only. Botanical characteristics were taken in March 2015 when the plants were 7 months old from seed. A sample size of 3 plants was used for each plant type and for each characteristic.

Table 1 compares the botanical characteristics of the dwarf pink-white lupine having the dwarf plant height characteristic, trait, or phenotype with the standard tall pink-white bi-color lupine. In Table 1, column one shows the botanical characteristics, columns two and three show the range and average for each characteristic of the dwarf pink-white bi-color, respectively, and columns five and six show the range and average for each characteristic of the tall Russell pink-white varieties, respectively. When comparing the plant height without raceme between the dwarf and tall, the dwarf plants were 47.6% shorter than the tall plants (an average height of 9 cm compared to the tall lupine having an average height of 17.17 cm). When comparing the plant height with raceme, the dwarf plants were 32.6% shorter than the tall plants (an average height of 33.5 cm compared to the tall lupine having an average height of 49.67 cm). When comparing the number of racemes per plant, the dwarf plants produced 74% more racemes than the tall plants (an average of 4.7 racemes compared to the tall lupine having an average of 2.7 racemes). When comparing the number of lateral branches per plant, the dwarf plant had 123% more lateral branches than the tall plants (an average of 6.7 lateral branches compared to the tall lupine having an average of 3 lateral branches). When comparing the number of leaves per plant, the dwarf plants had 78.4% more leaves per plant (an average of 27.3 leaves compared to the tall lupine having an average of 15.3 leaves).

TABLE 1

Pink-white bi-color dwarf and tall comparisons

| Characteristic | Dwarf pink-white bi-color | | Tall pink-white bi-color | |
| --- | --- | --- | --- | --- |
| | Range | Average | Range | Average |
| Plant height without raceme (cm) | 9 | 9 | 16.5-18 | 17.17 |
| Plant height with raceme (cm) | 29-34.5 | 33.5 | 42-54 | 49.67 |
| Plant width (cm) | 23-25 | 24.3 | 26-34 | 29.67 |
| Racemes per plant | 4-6 | 4.7 | 2-3 | 2.7 |
| Raceme spread or width (cm) | 6.5-7.5 | 6.8 | 6.5-8 | 7.3 |
| Raceme height (cm) | 20-29 | 24.8 | 25-37 | 32.3 |
| Florets per raceme | 120-136 | 130.7 | 112-172 | 136.7 |

TABLE 1-continued

Pink-white bi-color dwarf and tall comparisons

| Characteristic | Dwarf pink-white bi-color | | Tall pink-white bi-color | |
|---|---|---|---|---|
| | Range | Average | Range | Average |
| RHS color of florets, upper petal | 11D, 19D | Not applicable | 11D, 19D | Not applicable |
| RHS color of florets, lower petal | 63A, 63B | Not applicable | 55B, 63C, 72C | Not applicable |
| Peduncle length (cm) | 11-13 | 12 | 11-18 | 14.7 |
| Number of lateral branches per plant | 5-9 | 6.7 | 2-4 | 3 |
| Number of leaves per plant | 23-34 | 27.3 | 14-17 | 15.3 |
| Leaf length (cm) | 9-13 | 10.8 | 9-13 | 10.7 |
| Leaf width (cm) | 9.5-12.5 | 10.5 | 9.5-12 | 10.5 |
| Petiole length (cm) | 7.5-9 | 8.2 | 10-12 | 11.2 |
| Number of leaflets per leaf | 8-10 | 9 | 6-10 | 8.3 |
| Leaflet length (cm) | 5-6.5 | 5.7 | 5.6-7 | 6.4 |
| Leaflet width (cm) | 1.7-1.8 | 1.75 | 1.5-1.7 | 1.6 |

Figure 7:
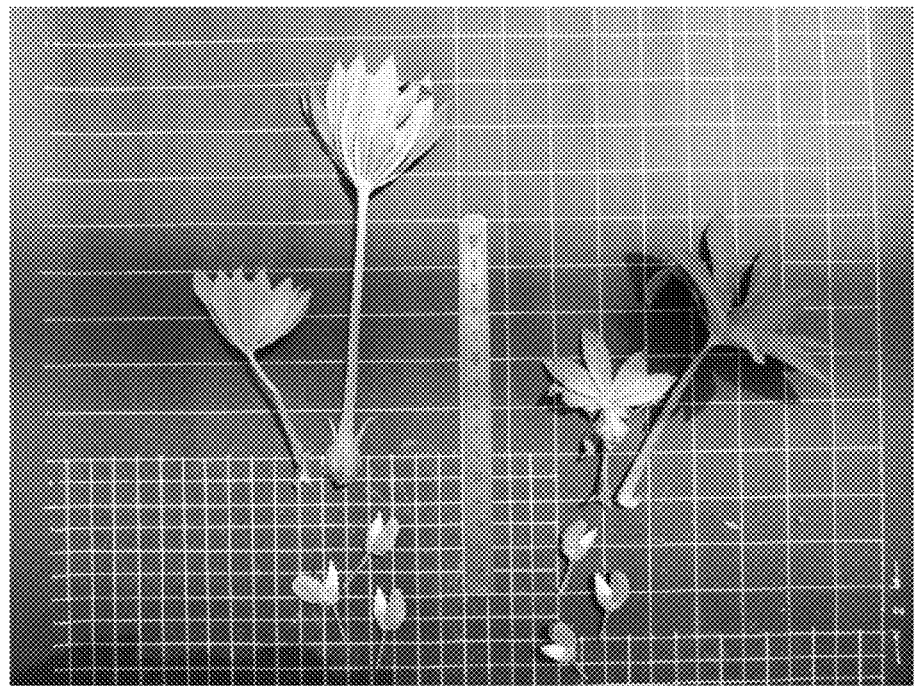
FIG. 7 is a photo comparing the immature leaves, leaflets, petioles, and individual florets between a tall Russell Reliance series pink-white bi-color plant on the left with a dwarf pink-white bi-color plant on the right. The plants are approximately 7 months old from seed.
Figure 8:
FIG. 8 is a photo comparing the overall plant habit and height between three Russell Reliance series pink-white bi-color plants on the left with three dwarf pink-white bi-color plants on the right. The plants are approximately 7 months old from seed.

FIGS. 7 and 8 compare the dwarf pink-white lupine having the dwarf plant height characteristic, trait, or phenotype with the standard tall pink-white bi-color lupine. As can be seen in FIG. 7 and above in Table 1, there is a marked difference in the petiole length of the leaf between the dwarf pink-white lupine with the standard tall pink-white bi-color lupine. The dwarf pink-white lupine has an average petiole length of 8.2 cm whereas the standard tall pink-white lupine has an average petiole length of 11.2 cm. In FIG. 8, the dwarf pink-white lupine plants are shown on the right, while the standard tall pink-white bi-color lupine are shown on the left. The dwarf varieties are significantly shorter and more compact in foliage height and raceme height than the standard tall pink-white bi-color lupine.

Table 2 compares the botanical characteristics of the dwarf blue-white lupine having the dwarf plant height characteristic, trait, or phenotype with the standard tall blue-white bi-color lupine. In Table 2, column one shows the botanical characteristics, columns two and three show the range and average for each characteristic of the dwarf blue-white bi-color, respectively, and columns five and six show the range and average for each characteristic of the tall Russell blue-white, respectively. When comparing the plant height without raceme between the dwarf and tall, on average, the dwarf plants were 61% shorter than the tall plants (an average of 7.8 cm when compared to the tall lupine having an average of 20 cm). When comparing the plant height with raceme, the dwarf plants were on average, 54.5% shorter than the tall plants (an average of 29 cm when compared to the tall lupine having an average of 51.3 cm). When comparing the number of racemes per plant, the dwarf plants produced on average, 43% more racemes than the tall plants (an average of 4.3 racemes per plant when compared the tall lupine having 1.3 racemes per plant). When comparing the number of lateral branches per plant, the dwarf plant had on average 67% more lateral branches than the tall plants (an average of 10 lateral branched per plant when compared to the tall lupine having 4 lateral branched per plant). When comparing the number of leaves per plant, the dwarf plants had on average, 124% more leaves per plant (an average of 34.3 leaves per plant compared to the tall lupine having 15.3 leaves per plant).

TABLE 2

Blue-white bi-color dwarf and tall comparison

| Characteristic | Dwarf blue-white bi-color | | Tall blue-white bi-color | |
|---|---|---|---|---|
| | Range | Average | Range | Average |
| Plant height without raceme (cm) | 5.5-9 | 7.8 | 15-27 | 20 |
| Plant height with raceme (cm) | 20-36 | 29 | 48-58 | 51.3 |
| Plant width (cm) | 19-24 | 21.3 | 26-31 | 25.7 |
| Racemes per plant | 4-5 | 4.3 | 1-2 | 1.3 |
| Raceme spread or width (cm) | 6-7 | 6.3 | 8-9 | 8.3 |
| Raceme height (cm) | 15.5-27 | 21.5 | 20-40 | 30.7 |
| Florets per raceme | 110-124 | 118 | 118-140 | 131.3 |
| RHS color of florets, upper petal | 4C, 4D | Not applicable | 4D, 11D | Not applicable |
| RHS color of florets, lower petal | 83A, 83B | Not applicable | 77A, 79C, 79B | Not applicable |
| Peduncle length (cm) | 10-14 | 12 | 15-20 | 16.7 |
| Number of lateral branches per plant | 9-11 | 10 | 2-7 | 4 |
| Number of leaves per plant | 31-38 | 34.3 | 9-22 | 15.3 |
| Leaf length (cm) | 8-11 | 9.3 | 11-12.5 | 11.8 |
| Leaf width (cm) | 8.5-11 | 9.5 | 11-14 | 12.3 |
| Petiole length (cm) | 5.5-10.5 | 7.8 | 10-12 | 11.2 |
| Number of leaflets per leaf | 9-10 | 9.3 | 9-12 | 10.3 |
| Leaflet length (cm) | 4.8-6 | 5.4 | 6.5-8 | 7.3 |
| Leaflet width (cm) | 1.6-1.8 | 1.7 | 1.6-1.7 | 1.7 |

Figure 5:
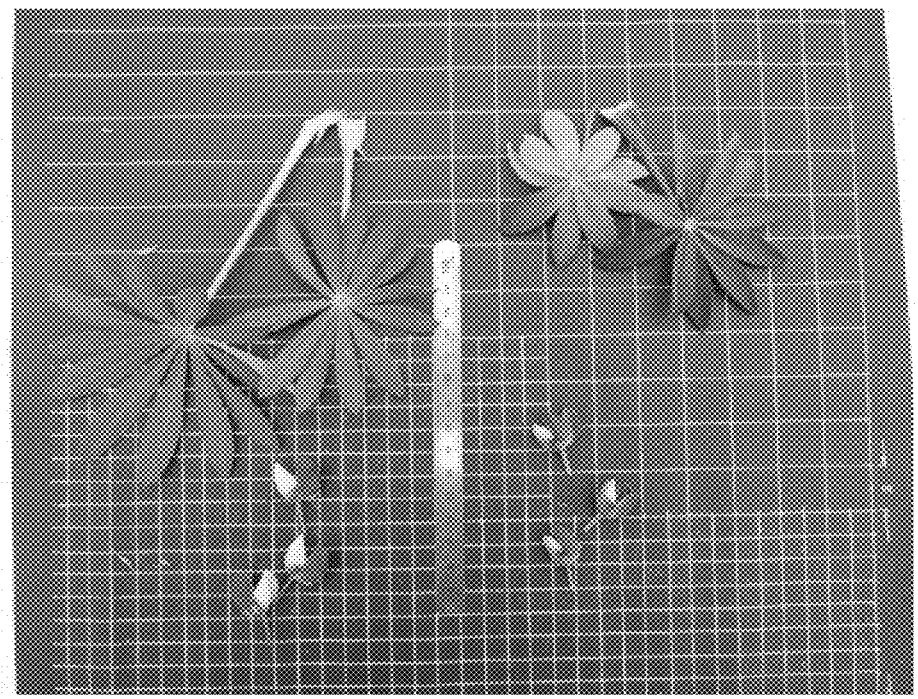
FIG. 5 is a photo comparing the immature leaves, leaflets, petioles, and individual florets between a tall Russell Reliance series blue-white bi-color plant on the left with a dwarf blue-white bi-color plant on the right. The plants are approximately 7 months old from seed.
Figure 6:
FIG. 6 is a photo comparing the overall plant habit and height between three tall Russell Reliance series blue-white bi-color plants on the left with three dwarf blue-white bi-color plants on the right. The plants are approximately 7 months old from seed.

FIGS. 5 and 6 compare the dwarf blue-white lupine with the standard tall blue-white bi-color lupine. As can be seen in FIG. 5 and in Table 2 above, there is a marked difference in the petiole length of the leaf between the dwarf blue-white lupine with the standard tall blue-white bi-color lupine. The dwarf blue-white lupine has an average petiole length of 7.8 cm whereas the standard tall blue-white lupine has an average petiole length of 11.2 cm. In FIG. 5, the dwarf blue-white lupine plants are shown on the right, while the standard tall blue-white bi-color lupine are shown on the left. The dwarf varieties are significantly shorter and more compact in foliage height and raceme height than the standard tall blue-white bi-color lupine.

Table 3 compares the botanical characteristics of the dwarf red lupine having the dwarf plant height characteristic, trait, or phenotype with the standard tall red lupine. In Table 3, column one shows the botanical characteristics, columns two and three show the range and average for each characteristic of the dwarf red, respectively, and columns five and six show the range and average for each characteristic of the tall Russell red respectively. When comparing the plant height without raceme between the dwarf and tall, on average, the dwarf plants were 93.7% shorter than the tall plants (an average of 8.5 cm when compared to the tall lupine having an average of 15.8 cm). When comparing the plant height with raceme, the dwarf plants were on average, 16.8% shorter than the tall plants (an average of 32.3 cm when compared to the tall lupine having an average of 38.8 cm). When comparing the number of racemes per plant, the dwarf plants produced on average, 32.5% more racemes than the tall plants (an average of 5.3 racemes per plant when compared to the tall lupine having an average of 4 racemes per plant). When comparing the number of lateral branches per plant, the dwarf plant had on average 107.5% more lateral branches than the tall plants (an average of 8.3 lateral branches per plant compared to the tall lupine having an average of 4 lateral branches per plant). When comparing the number of leaves per plant, the dwarf plants had on average, 63.5% more leaves per plant (an average of 32.7 leaves per plant compared to the tall lupine having an average of 20 leaves per plant).

TABLE 3

Red dwarf and tall comparison

| Characteristic | Dwarf red | | Tall red | |
| --- | --- | --- | --- | --- |
| | Range | Average | Range | Average |
| Plant height without raceme (cm) | 8.5-9 | 8.5 | 14.5-17 | 15.8 |
| Plant height with raceme (cm) | 31-34 | 32.3 | 36-41.5 | 38.8 |
| Plant width (cm) | 21-26 | 24 | 31-38 | 34 |
| Racemes per plant | 3-7 | 5.3 | 3-5 | 4 |
| Raceme spread or width (cm) | 7-7.2 | 7.1 | 7-7.5 | 7.2 |
| Raceme height (cm) | 23-24.5 | 23.8 | 21-26 | 23 |
| Florets per raceme | 120-144 | 128 | 124-128 | 125 |
| RHS color of florets, upper petal | 58A, 59D, 60D | Not applicable | 64A, 71B | Not applicable |
| RHS color of florets, lower petal | 63A, 63B | Not applicable | 61D, 63A | Not applicable |
| Peduncle length (cm) | 12-13 | 12.3 | 13-15 | 13.7 |
| Number of lateral branches per plant | 7-10 | 8.3 | 3-6 | 4 |
| Number of leaves per plant | 27-36 | 32.7 | 16-27 | 20 |
| Leaf length (cm) | 9-10 | 9.5 | 12-13 | 12.3 |
| Leaf width (cm) | 8.5-9 | 8.8 | 12-13 | 12.5 |
| Petiole length (cm) | 7.5-8 | 7.7 | 11.5-24 | 16.2 |
| Number of leaflets per leaf | 7-10 | 9 | 8-10 | 9 |
| Leaflet length (cm) | 5.5-6 | 5.7 | 7.3-9.5 | 8.1 |

Figure 2:
FIG. 2 is a photo comparing the overall plant habit and height between three tall Russell Reliance red plants on the left with three dwarf red plants on the right. The plants are approximately 7 months old from seed.

FIGS. 1 and 2 compare the dwarf red lupine with the standard tall red lupine. As can be seen in FIG. 1, there is a marked difference in the petiole length of the leaf between the dwarf red lupine with the standard tall red lupine. The dwarf red lupine has an average petiole length of 7.7 cm whereas the standard tall red lupine has an average petiole length of 16.2 cm. In FIG. 2, the dwarf red lupine plants are shown on the right, while the standard tall red lupine are shown on the left. The dwarf varieties are significantly shorter and more compact in foliage height and raceme height than the standard tall red lupine.

Table 4 compares the botanical characteristics of the dwarf yellow lupine having the dwarf plant height characteristic, trait, or phenotype with the standard tall yellow lupine. In Table 4, column one shows the botanical characteristics, columns two and three show the range and average for each characteristic of the dwarf yellow respectively, and columns five and six show the range and average for each characteristic of the tall Russell yellow respectively. When comparing the plant height without raceme between the dwarf and tall, on average, the dwarf plants were 39.2% shorter than the tall plants (an average of 8.7 cm when compared to the tall lupine having an average of 14.3 cm). When comparing the plant height with raceme, the dwarf plants were on average, 40.6% shorter than the tall plants (an average of 25.7 cm when compared to the tall lupine having an average of 43.3 cm). When comparing the number of racemes per plant, the dwarf plants produced on average, 60.9% more racemes than the tall plants (an average of 3.7 racemes per plant when compared to the tall lupine having an average of 2.3 racemes per plant). When comparing the number of lateral branches per plant, the dwarf plant had on average 200% more lateral branches than the tall plants (an average of 9 lateral branches per plant when compared to the tall lupine having 3 lateral branches per plant). When comparing the number of leaves per plant, the dwarf plants had on average, 70.9% more leaves per plant (an average of 21.7 leaves per plant compared to the tall lupine having an average of 12.7 leaves per plant).

TABLE 4

Yellow dwarf and tall comparison

| Characteristic | Dwarf yellow | | Tall yellow | |
| --- | --- | --- | --- | --- |
| | Range | Average | Range | Average |
| Plant height without raceme (cm) | 8-9 | 8.7 | 13-17 | 14.3 |
| Plant height with raceme (cm) | 21-30 | 25.7 | 41-45 | 43.3 |
| Plant width (cm) | 23-26 | 24.3 | 28-34 | 30.7 |
| Racemes per plant | 2-5 | 3.7 | 1-4 | 2.3 |
| Raceme spread or width (cm) | 6.5-7 | 6.7 | 9-18 | 15 |
| Raceme height (cm) | 19-23 | 21.3 | 27-33 | 29.3 |
| Florets per raceme | 104-136 | 120 | 126-171 | 141 |
| RHS color of florets, upper petal | 5A, 7A, 9B | Not applicable | 6B, 7C | Not applicable |
| RHS color of florets, lower petal | 10B, 10C | Not applicable | 10A, 10C | Not applicable |
| Peduncle length (cm) | 10-16 | 12.7 | 18-19 | 18.3 |
| Number of lateral branches per plant | 6-9 | 9 | 2-4 | 3 |
| Number of leaves per plant | 20-24 | 21.7 | 10-17 | 12.7 |
| Leaf length (cm) | 9-11 | 10.3 | 11-13 | 12 |
| Leaf width (cm) | 9-10 | 9.3 | 12-13 | 12.3 |
| Number of leaflets per leaf | 9-10 | 9.7 | 11 | 11 |
| Leaflet length (cm) | 5.5-5.6 | 5.5 | 7-8.3 | 7.4 |
| Leaflet width (cm) | 1.4-1.8 | 1.6 | 1.7-2.1 | 1.9 |

Figure 3:
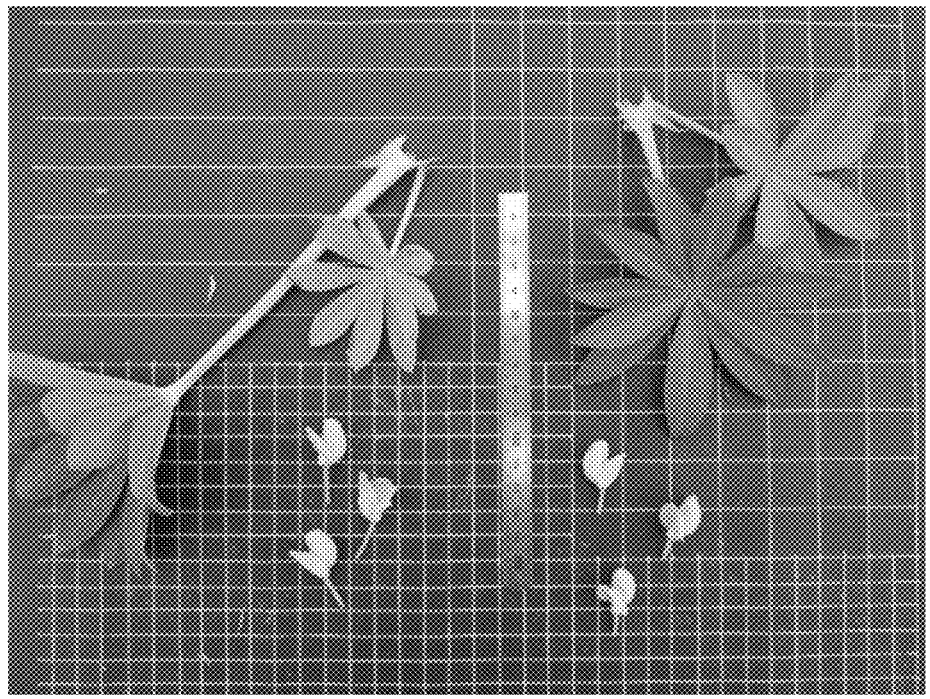
FIG. 3 is a photo comparing the immature leaves, leaflets, petioles, and individual florets between a tall Russell Reliance series yellow plant on the left with a dwarf yellow plant on the right. The plants are approximately 7 months old from seed.
Figure 4:
FIG. 4 is a photo comparing the overall plant habit and height between three tall Russell Reliance yellow plants on the left with three dwarf yellow plants on the right. The plants are approximately 7 months old from seed.

FIGS. 3 and 4 compare the dwarf yellow lupine with the standard tall yellow lupine. As can be seen in FIG. 3, there is a marked difference in the petiole length of the leaf between the dwarf yellow lupine with the standard tall yellow lupine. In FIG. 4, the dwarf yellow lupine plants are shown on the right, while the standard tall yellow lupine are shown on the left. The dwarf varieties are significantly shorter and more compact in foliage height and raceme height than the standard tall yellow lupine.

Table 5 shows the ranges and averages of the characteristics for all colors for all dwarf lupine plants having the dwarf plant height characteristic, trait, or phenotype and tall lupine plants taken from Tables 1 to 4. In Table 5, column one shows the botanical characteristics, columns two and three show the range and range in averages for each characteristic of the dwarf lupine plants respectively, and columns five and six show the range and the range in averages for each characteristic of the tall plants respectively.

TABLE 5

Dwarf and tall comparisons for all colors

| Characteristic | Dwarf | | Tall | |
| --- | --- | --- | --- | --- |
| | Range | Average | Range | Average |
| Plant height without raceme (cm) | 5-9 | 7.8-9 | 13-27 | 14.3-20 |
| Plant height with raceme (cm) | 20-36 | 25.7-33.5 | 36-58 | 38.8-51.3 |
| Plant width (cm) | 19-26 | 21.3-24 | 26-38 | 25.7-34 |
| Racemes per plant | 2-7 | 3.7-6.3 | 1-5 | 1.3-4 |
| Raceme spread or width (cm) | 6-7.5 | 6.3-7.1 | 6.5-18 | 7.2-15 |

TABLE 5-continued

Dwarf and tall comparisons for all colors

| Characteristic | Dwarf | | Tall | |
| --- | --- | --- | --- | --- |
| | Range | Average | Range | Average |
| Raceme height (cm) | 15.5-29 | 21.3-24.8 | 20-40 | 23-32.3 |
| Florets per raceme | 104-144 | 125-141 | 112-172 | 125-136.7 |
| Peduncle length (cm) | 10-16 | 12-12.7 | 11-20 | 13.7-18.3 |
| Number of lateral branches per plant | 5-11 | 6.7-10 | 2-7 | 3-4 |
| Number of leaves per plant | 20-38 | 21.7-34.3 | 9-27 | 12.7-20 |
| Leaf length (cm) | 8-13 | 9.3-10.8 | 9-13 | 10-7-12.3 |
| Leaf width (cm) | 8.5-12.5 | 8.8-10.5 | 9.5-14 | 10.5-12.5 |
| Petiole length (cm) | 5.5-10.5 | 7.7-8.2 | 10-24 | 11.2-16.2 |
| Number of leaflets per leaf | 8-10 | 9-9.7 | 6-11 | 8.3-11 |
| Leaflet length (cm) | 4.8-6.5 | 5.4-5.7 | 5.6-9.5 | 6.4-8.1 |
| Leaflet width (cm) | 1.4-1.8 | 1.6-1.75 | 1.5-2.1 | 1.6-1.9 |

Figure 9:
FIG. 9 is a photo comparing the overall plant habit and height between a tall Russell Reliance series on the left with a dwarf plant on the right. As can be shown from the photo, there is a significant difference in plant height and width between the two plants. Both plants are shown with immature racemes. The plants are approximately 7 months old from seed.

FIG. 9 is a photo comparing the overall plant habit and height between a tall Russell Reliance series on the left with a dwarf lupine having the dwarf plant height characteristic, trait, or phenotype on the right. As can be shown from the photo, there is a significant difference in plant height and width between the two plants. Both plants are shown with immature racemes. The plants are approximately 7 months old from seed.

Figure 10:
FIG. 10 is a photo of a multiple plants of various colors of the dwarf lupine blooming in a greenhouse. The plants are approximately 7 months old from seed.
Figure 11:
FIG. 11 is a photo of multiple plants of various colors of the tall Russell Reliance series lupine blooming in a greenhouse. The plants are approximately 7 months old from seed.
Figure 12:
FIG. 12 is a photo of the dwarf lupine plants shown with the tall Russell Reliance series blooming in a greenhouse. The dwarf lupine plants are in the left front part of the photo. The plants are approximately 7 months old from seed.
Figure 13:
FIG. 13 is a photo of the red dwarf lupine plants in a group.
Figure 14:
FIG. 14 is a photo of the bi-color dwarf lupine blue and white plants in a group.
Figure 15:
FIG. 15 is a photo of the yellow dwarf lupine plants in group.
Figure 16:
FIG. 16 is a photo of the dwarf lupine pink-white bi-color plants in a group.

FIG. 10 to FIG. 12 are photos of multiple plant comparisons between the dwarf lupine having the dwarf plant height characteristic, trait, or phenotype with the tall Russell lupine plants. FIG. 10 is a photo of a multiple plants of various colors of the dwarf lupine blooming in a greenhouse. The plants are approximately 7 months old from seed. FIG. 11 is a photo of multiple plants of various colors of the tall Russell Reliance series lupine blooming in a greenhouse. The plants are approximately 7 months old from seed. FIG. 12 is a photo of the dwarf lupine plants shown with the tall Russell Reliance series blooming in a greenhouse. The dwarf lupine plants are in the left front part of the photo. The plants are approximately 7 months old from seed. FIG. 10 to FIG. 12 clearly show a marked difference in plant height between the dwarf lupine having the dwarf plant height characteristic, trait, or phenotype with the tall Russell lupine plants. FIGS. 13 to 16 show the various dwarf individual colors in a group (en mass).

3. Crosses of Dwarf Lupine Having the Dwarf Plant Height Characteristic, Trait, or Phenotype with Other Lupine-Interspecific Crosses of Lupine As shown by the breeding history and data, the dwarf lupine height characteristic, trait, or phenotype (i.e., very short plant height) is a heritable trait and can be bred into other lupine plants. When in the homozygous form, lupine plants will exhibit the dwarf plant height phenotype, characteristic, or trait. Interspecific crosses in lupine are well-known in the art. Please see Bragdo, Marie, "Interspecific Crosses in *Lupinus* Cytology and Inheritance in Flower Color", Hereditas, 43 (2): 338-356, July 1957.

For example, a dwarf *Lupinus polyphyllus* hybrid plant homozygous recessive for the dwarf mutant allele, wherein a representative sample of seed containing said allele was deposited under NCIMB No. 42442, may be bred with at least one other *Lupinus* species such as *polyphyllus, arboreus, sulphureus*, and *nootkatensis* to produce at least one interspecific hybrid seed; harvesting the interspecific hybrid seed and germinating the interspecific hybrid seed can produce progeny interspecific *Lupinus* hybrid plants.

Further Embodiments

Characterization of the Dwarf Lupine Recessive Allele Using Complementation Assays The recessive allele responsible for the very short plant height of the lupine of the present application can be identified using complementation assays, which are well-known in the art. See for example, Griffiths et al. "An Introduction to Genetic Analysis" $7^{th}$ Edition. W.H. Freeman (2000), explaining how a mutant condition that is determined by a recessive allele can be determined.

Breeding with Dwarf Lupine

The goal of ornamental plant breeding is to develop new, unique and superior ornamental varieties and hybrids. The breeder initially selects and crosses two or more parental lines, followed by repeated selfing and selection, producing many new genetic combinations. The breeder can theoretically generate billions of different genetic combinations via crossing, selection, selfing and mutations. Therefore, a breeder will never develop the same variety genetically and having the same traits from the exact same parents.

Each year, the plant breeder selects the germplasm to advance to the next generation. This germplasm is grown under unique and different geographical, climatic and soil conditions and further selections are then made during and at the end of the growing season. The varieties that are developed are unpredictable because the breeder's selection occurs in unique environments with no control at the DNA level, and with millions of different possible genetic combinations being generated. A breeder of ordinary skill in the art cannot predict the final resulting lines he develops, except possibly in a very gross and general fashion. The same breeder cannot produce the same variety twice by using the same original parents and the same selection techniques. This unpredictability results in the expenditure of large amounts of research monies to develop superior new lupine varieties.

Breeding programs combine desirable traits from two or more varieties or various broad-based sources into breeding pools from which varieties are developed by selfing and selection of desired phenotypes. Pedigree breeding is used commonly for the improvement of self-pollinating plants. Two parents that possess favorable, complementary traits are crossed to produce an $F_1$. An $F_2$ population is produced by selfing one or several $F_1$s. Selection of the best individuals may begin in the $F_2$ population; then, beginning in the $F_3$, the best individuals in the best families are selected. Replicated testing of families can begin in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new varieties.

Using Dwarf Lupine to Develop Other Lupine Plants

Lupine, such as the dwarf lupine are developed for sales in the ornamental and cut flower market. However, said lupine plants can also provide a source of breeding material that may be used to develop new lupine plants and varieties. Plant breeding techniques known in the art and used in a lupine plant breeding program include, but are not limited to, recurrent selection, mass selection, bulk selection, hybridization, mass selection, backcrossing, pedigree breeding, open-pollination breeding, restriction fragment length polymorphism enhanced selection, genetic marker enhanced selection, making double haploids, mutagenesis and transformation. Often combinations of these techniques are used. The development of lupine varieties in a plant breeding program requires, in general, the development and evaluation of homozygous varieties. There are many analytical methods available to evaluate a new variety. The oldest and most traditional method of analysis is the observation of phenotypic traits, but genotypic analysis may also be used.

Additional Breeding Methods

Any plants produced using the lupine plants disclosed in the present application as at least one parent are also an embodiment. These methods are well-known in the art and some of the more commonly used breeding methods are described herein. Descriptions of breeding methods can be found in one of several reference books (e.g., Allard, "Principles of Plant Breeding" (1999); Vainstein, "Breeding for Ornamentals: Classical and Molecular Approaches," Kluwer Academic Publishers (2002); Callaway, "Breeding Ornamental Plants," Timber Press (2000); and Bragdø, Marie, "Inter-specific Crosses in Lupinus: Cytology and Inheritance of Flower Color," Institute of Genetics and Plant Breeding, Agricultural College of Norway, Vollebekk, Norway (Sep. 28, 1956).

Breeding steps that may be used in the Lupine plant breeding program can include for example, pedigree breeding, backcrossing, mutation breeding, and recurrent selection. In conjunction with these steps, techniques such as RFLP-enhanced selection, genetic marker enhanced selection (for example, SSR markers), and the making of double haploids may be utilized.

As used herein, the term "plant" includes plant cells, plant protoplasts, plant cell tissue cultures from which Lupine plants can be regenerated, plant calli, plant clumps, and plant cells that are intact in plants or parts of plants, such as pollen, ovules, embryos, protoplasts, meristematic cells, callus, pollen, leaves, ovules, anthers, cotyledons, hypocotyl, pistils, roots, root tips, seeds, flowers, petiole, pods, shoot, or stems and the like.

Pedigree Breeding

Pedigree breeding starts with the crossing of two genotypes, such as dwarf lupine and another different lupine having one or more desirable characteristics that is lacking or which complements the dwarf lupine phenotype. If the two original parents do not provide all the desired characteristics, other sources can be included in the breeding population. In the pedigree method, superior plants are selfed and selected in successive filial generations. In the succeeding filial generations, the heterozygous condition gives way to homogeneous varieties as a result of self-pollination and selection. Typically in the pedigree method of breeding, five or more successive filial generations of selfing and selection is practiced: $F_1$ to $F_2$; $F_2$ to $F_3$; $F_3$ to $F_4$; $F_4$ to $F_5$; etc. After a sufficient amount of inbreeding, successive filial generations will serve to increase seed of the developed variety. Preferably, the developed variety comprises homozygous alleles at about 95% or more of its loci.

Backcross Breeding

Backcross breeding has been used to transfer genes for a simply inherited, highly heritable trait into a desirable homozygous variety or inbred line which is the recurrent parent. The source of the trait to be transferred is called the donor parent. After the initial cross, individuals possessing the phenotype of the donor parent are selected and repeatedly crossed (backcrossed) to the recurrent parent. The resulting plant is expected to have the attributes of the recurrent parent and the desirable trait transferred from the donor parent.

In addition to being used to create a backcross conversion, backcrossing can also be used in combination with pedigree breeding. As discussed previously, backcrossing can be used to transfer one or more specifically desirable traits from one variety, the donor parent, to a developed variety called the recurrent parent, which has overall good commercial characteristics yet lacks that desirable trait or traits. However, the same procedure can be used to move the progeny toward the genotype of the recurrent parent, but at the same time retain many components of the nonrecurrent parent by stopping the backcrossing at an early stage and proceeding with selfing and selection. For example, a Lupine plant may be crossed with another variety to produce a first generation progeny plant. The first generation progeny plant may then be backcrossed to one of its parent varieties to create a $BC_1$ or $BC_2$. Progeny are selfed and selected so that the newly developed variety has many of the attributes of the recurrent parent and yet several of the desired attributes of the nonrecurrent parent. This approach leverages the value and strengths of the recurrent parent for use in new Lupine varieties.

Therefore, another embodiment is a method of making a backcross conversion of dwarf lupine, comprising the steps of crossing a plant of dwarf lupine with a donor plant comprising a desired trait, selecting an $F_1$ progeny plant comprising the desired trait, and backcrossing the selected $F_1$ progeny plant to a plant of dwarf lupine. This method may further comprise the step of obtaining a molecular marker profile of dwarf lupine and using the molecular marker profile to select for a progeny plant with the desired trait and the molecular marker profile of dwarf lupine.

Recurrent Selection and Mass Selection

Recurrent selection is a method used in a plant breeding program to improve a population of plants. Dwarf lupine are suitable for use in a recurrent selection program. The method entails individual plants cross-pollinating with each other to form progeny. The progeny are grown and the superior progeny selected by any number of selection methods, which include individual plant, half-sib progeny, full-sib progeny, and selfed progeny. The selected progeny are cross-pollinated with each other to form progeny for another population. This population is planted and again superior plants are selected to cross-pollinate with each other. Recurrent selection is a cyclical process and therefore can be repeated as many times as desired. The objective of recurrent selection is to improve the traits of a population. The improved population can then be used as a source of breeding material to obtain new varieties for commercial or breeding use, including the production of a synthetic variety. A synthetic variety is the resultant progeny formed by the intercrossing of several selected varieties.

Mass selection is a useful technique when used in conjunction with molecular marker enhanced selection. In mass selection, seeds from individuals are selected based on phenotype or genotype. These selected seeds are then bulked and used to grow the next generation. Bulk selection requires growing a population of plants in a bulk plot, allowing the plants to self-pollinate, harvesting the seed in bulk, and then using a sample of the seed harvested in bulk to plant the next generation. Also, instead of self-pollination, directed pollination could be used as part of the breeding program.

Mass and recurrent selections can be used to improve populations of either self- or cross-pollinating plants. A genetically variable population of heterozygous individuals is either identified, or created, by intercrossing several different parents. The best plants are selected based on individual superiority, outstanding progeny, or excellent combining ability. The selected plants are intercrossed to produce a new population in which further cycles of selection are continued.

Mutation Breeding

Mutation breeding is another method of introducing new traits into dwarf Lupine. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation; such as X-rays, Gamma rays (e.g., cobalt 60 or cesium 137), neutrons, (product of nuclear fission by uranium 235 in an atomic reactor), Beta radiation (emitted from radioisotopes such as phosphorus 32 or carbon 14), or ultraviolet radiation (preferably from 2500 to 2900 nm), or chemical mutagens (such as base analogues (5-bromo-uracil)), related compounds (8-ethoxy caffeine), antibiotics (streptonigrin), alkylating agents (sulfur mustards, nitrogen mustards, epoxides, ethylenamines, sulfates, sulfonates, sulfones, lactones), azide, hydroxylamine, nitrous acid, or acridines. Once a desired trait is observed through mutagenesis the trait may then be incorporated into existing germplasm by traditional breeding techniques. Details of mutation breeding can be found in Vainstein, "Breeding for Ornamentals: Classical and Molecular Approaches," Kluwer Academic Publishers (2002). In addition, mutations created in other Lupine plants may be used to produce a backcross conversion of dwarf Lupine that comprises such mutation.

Additional methods include, but are not limited to, expression vectors introduced into plant tissues using a direct gene transfer method, such as microprojectile-mediated delivery, DNA injection, electroporation, and the like. More preferably, expression vectors are introduced into plant tissues by using either microprojectile-mediated delivery with a biolistic device or by using *Agrobacterium*-mediated transformation. Transformant plants obtained with the protoplasm of the subject lupine plants are intended to be within the scope of the embodiments of the application.

Single-Gene Conversions

When the term lupine plant is used in the context of an embodiment of the present application, this also includes any single gene conversions of dwarf lupine. The term single gene converted plant as used herein refers to those lupine plants which are developed by a plant breeding technique called backcrossing wherein essentially all of the desired morphological and physiological characteristics of a variety are recovered in addition to the single gene transferred into the variety via the backcrossing technique. Backcrossing methods can be used with one embodiment of the present application to improve or introduce a characteristic into the variety. The term "backcrossing" as used herein refers to the repeated crossing of a hybrid progeny back to the recurrent parent, i.e., backcrossing 1, 2, 3, 4, 5, 6, 7, 8, or more times to the recurrent parent. The parental lupine plant that contributes the gene for the desired characteristic is termed the nonrecurrent or donor parent. This terminology refers to the fact that the nonrecurrent parent is used one time in the backcross protocol and therefore does not recur. The parental Lupine plant to which the gene or genes from the nonrecurrent parent are transferred is known as the recurrent parent as it is used for several rounds in the backcrossing protocol (Poehlman & Sleper (1994). In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a lupine plant is obtained wherein essentially all of the desired morphological and physiological characteristics of the recurrent parent are recovered in the converted plant, in addition to the single transferred gene from the nonrecurrent parent.

The selection of a suitable recurrent parent is an important step for a successful backcrossing procedure. The goal of a backcross protocol is to alter or substitute a single trait or characteristic in the original variety. To accomplish this, a single gene of the recurrent variety is modified or substituted with the desired gene from the nonrecurrent parent, while retaining essentially all of the rest of the desired genetic, and therefore the desired physiological and morphological constitution of the original variety. The choice of the particular nonrecurrent parent will depend on the purpose of the backcross; one of the major purposes is to add some commercially important trait or traits to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single gene traits have been identified that are not regularly selected for in the development of a new variety but that can be improved by backcrossing techniques. These traits are well-known in the art.

Introduction of a New Trait or Locus into Dwarf Lupine

Dwarf lupine represents a new base of genetics into which a new locus or trait may be introgressed. Direct transformation and backcrossing represent two important methods that can be used to accomplish such an introgression. The term backcross conversion and single locus conversion are used interchangeably to designate the product of a backcrossing program.

Backcross Conversions of Dwarf Lupine

A backcross conversion of dwarf lupine occurs when DNA sequences are introduced through backcrossing (Allard, "Principles of Plant Breeding" (1999) with Dwarf Lupine utilized as the recurrent parent. Both naturally occurring and transgenic DNA sequences may be introduced through backcrossing techniques. A backcross conversion may produce a plant with a trait or locus conversion in at least two or more backcrosses, including at least 2 crosses, at least 3 crosses, at least 4 crosses, at least 5 crosses, and the like. Molecular marker assisted breeding or selection may be utilized to reduce the number of backcrosses necessary to achieve the backcross conversion. For example, see, Openshaw, S. J., et al., Marker-assisted Selection in Backcross Breeding, Proceedings Symposium of the Analysis of Molecular Data, *Crop Science Society of America*, Corvallis, Oreg. (August 1994), where it is demonstrated that a backcross conversion can be made in as few as two backcrosses.

The complexity of the backcross conversion method depends on the type of trait being transferred (single genes or closely linked genes as compared to unlinked genes), the level of expression of the trait, the type of inheritance (cytoplasmic or nuclear), and the types of parents included in the cross. It is understood by those of ordinary skill in the art that for single gene traits that are relatively easy to classify, the backcross method is effective and relatively easy to manage. See, Allard, "Principles of Plant Breeding" (1999). Desired traits that may be transferred through backcross conversion include, but are not limited to, sterility (nuclear and cytoplasmic), fertility restoration, drought tolerance, nitrogen utilization, ornamental features, disease resistance (bacterial, fungal, or viral), insect resistance, and herbicide resistance. In addition, an introgression site itself, such as an FRT site, Lox site, or other site specific integration site, may be inserted by backcrossing and utilized for direct insertion of one or more genes of interest into a specific plant variety. In some embodiments, the number of loci that may be backcrossed into Dwarf Lupine is at least 1, 2, 3, 4, or 5, and/or no more than 6, 5, 4, 3, or 2. A single locus may contain several transgenes, such as a transgene for disease resistance that, in the same expression vector, also contains a transgene for herbicide resistance. The gene for herbicide resistance may be used as a selectable marker and/or as a phenotypic trait. A single locus conversion of site specific integration system allows for the integration of multiple genes at the converted loci.

The backcross conversion may result from either the transfer of a dominant allele or a recessive allele. Selection of progeny containing the trait of interest is accomplished by direct selection for a trait associated with a dominant allele. Transgenes or genes transferred via backcrossing typically function as a dominant single gene trait and are relatively easy to classify. Selection of progeny for a trait that is transferred via a recessive allele requires growing and selfing the first backcross generation to determine which plants carry the recessive alleles. Recessive traits may require additional progeny testing in successive backcross generations to determine the presence of the locus of interest. The last backcross generation is usually selfed to give pure breeding progeny for the gene(s) being transferred, although a backcross conversion with a stably introgressed trait may also be maintained by further backcrossing to the recurrent parent with selection for the converted trait.

In addition, the above process and other similar processes described herein may be used to produce first generation progeny lupine seed by adding a step at the end of the process that comprises crossing Dwarf lupine with the introgressed trait or locus with a different Lupine plant and harvesting the resultant first generation progeny Lupine seed.

Molecular Techniques Using Dwarf Lupine

The advent of new molecular biological techniques has allowed the isolation and characterization of genetic elements with specific functions. Traditional plant breeding has principally been the source of new germplasm, however, advances in molecular technologies have allowed breeders to provide varieties with novel and much wanted commercial attributes. Molecular techniques such as transformation are popular in breeding ornamental plants and well-known in the art. See Vainstein, "Breeding for Ornamentals: Classical and Molecular Approaches," Kluwer Academic Publishers (2002).

Breeding with Molecular Markers

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select for the genome of the recurrent parent and against the genome of the donor parent. Using this procedure can minimize the amount of genome from the donor parent that remains in the selected plants. It can also be used to reduce the number of crosses back to the recurrent parent needed in a backcrossing program. The use of molecular markers in the selection process is often called genetic marker enhanced selection. Molecular markers may also be used to identify and exclude certain sources of germplasm as parental varieties or ancestors of a plant by providing a means of tracking genetic profiles through crosses. Molecular markers, which includes markers identified through the use of techniques such as Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs), and Single Nucleotide Polymorphisms (SNPs), may be used in plant breeding methods utilizing Dwarf Lupine. See Vainstein, "Breeding for Ornamentals: Classical and Molecular Approaches," Kluwer Academic Publishers (2002).

Genetic Marker Profile Through SSR and First Generation Progeny

In addition to phenotypic observations, a plant can also be identified by its genotype. The genotype of a plant can be characterized through a genetic marker profile which can identify plants of the same variety, or a related variety, or be used to determine or validate a pedigree. Genetic marker profiles can be obtained by techniques such as Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) (which are also referred to as Microsatellites), and Single Nucleotide Polymorphisms (SNPs), all of which are well-known in the art.

Tissue Culture

Further reproduction of the variety can occur by tissue culture and regeneration. Tissue culture of various tissues of ornamental plants and Lupine and regeneration of plants therefrom is well-known and widely published. For example, reference may be had to do Valla Rego, Luciana et al., Crop Breeding and Applied Technology. 1(3): 283-300 (2001); Komatsuda, T., et al., *Crop Sci.*, 31:333-337 (1991); Stephens, P. A., et al., *Theor. Appl. Genet.*, 82:633-635 (1991); Komatsuda, T., et al., *Plant Cell, Tissue and Organ Culture*, 28:103-113 (1992); Dhir, S., et al., *Plant Cell Reports*, 11:285-289 (1992); Pandey, P., et al., *Japan J. Breed.*, 42:1-5 (1992); and Shetty, K., et al., *Plant Science*, 81:245-251 (1992). Thus, another embodiment is to provide cells which upon growth and differentiation produce Lupine plants having the physiological and morphological characteristics of Dwarf lupine described in the present application.

Regeneration refers to the development of a plant from tissue culture. The term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as pollen, ovules, embryos, protoplasts, meristematic cells, callus, pollen, leaves, ovules, anthers, cotyledons, hypocotyl, pistils, roots, root tips, flowers, seeds, petiole, pods, shoot, or stems, and the like. Means for preparing and maintaining plant tissue culture are well-known in the art.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions, and sub-combinations as are within their true spirit and scope.

One or more aspects may be embodied in other specific forms without departing from its spirit or essential characteristics. The described embodiments are to be considered in all respects only as illustrative and not restrictive. The scope of the embodiments is, therefore, indicated by the appended claims rather than by the foregoing description. All changes which come within the meaning and range of equivalency of the claims are to be embraced within their scope. The foregoing discussion of the embodiments has been presented for purposes of illustration and description. The foregoing is not intended to limit the embodiments to the form or forms disclosed herein. In the foregoing Detailed Description for example, various features of the embodiments are grouped together in one or more embodiments for the purpose of streamlining the disclosure. This method of disclosure is not to be interpreted as reflecting an intention that the claimed embodiments require more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment.

Moreover, though the description of the embodiments has included description of one or more embodiments and certain variations and modifications, other variations and modifications are within the scope of the embodiments (e.g., as may be within the skill and knowledge of those in the art, after understanding the present disclosure). It is intended to obtain rights which include alternative embodiments to the extent permitted, including alternate, interchangeable and/or equivalent structures, functions, ranges or acts to those claimed, whether or not such alternate, interchangeable and/or equivalent structures, functions, ranges or acts are disclosed herein, and without intending to publicly dedicate any patentable subject matter.

The use of the terms "a," "an," and "the," and similar referents in the context of describing the embodiments (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the embodiments unless otherwise claimed. No language in the specification should be construed as indicating any non-claimed element as essential to the practice one or more embodiments.

DEPOSIT INFORMATION

A representative sample of a mixture of proprietary lupine seed of the Green Fuse Botanicals, Inc. comprising a homozygous recessive Tall gene that produces a dwarf plant height characteristic, wherein said deposit is designated LMISE08-0 and wherein said dwarf lupine plants grown from said seed display a dwarf plant height characteristic have been made with the National Collections of Industrial, Food and Marine Bacteria (NCIMB), Ferguson Building, Craibstone Estate, Bucksburn, Aberdeen, Scotland, AB21 9YA, United Kingdom. The date of deposit was Jul. 23, 2015 and the NCIMB No. is 42442. The deposit of 2,500 seeds wherein said lupine plants display a dwarf plant height characteristic was taken from the same deposit maintained by Green Fuse Botanicals, Inc. since prior to the filing date of this application. Upon issuance of a patent, all restrictions on the availability to the public of the deposit will be irrevocably removed consistent with all of the requirements of 37 C.F.R. §§1.801-1.809. The deposit will be maintained in the depository for a period of thirty years, or five years after the last request, or for the enforceable life of the patent, whichever is longer, and will be replaced as necessary during the period.

What is claimed is:

1. A lupine plant, wherein the genome of said lupine plant is comprised of one or more species, and wherein said species is selected from *Lupinus polyphyllus, Lupinus arboreus, Lupinus sulphureus*, and *Lupinus nooktatensis*, and wherein said plant comprises a recessive Tall gene that when in a homozygous state, produces a dwarf plant height characteristic, wherein said dwarf plant height characteristic comprises a lupine plant having a plant height with raceme of less than 35.0 cm, wherein a representative sample of seed of said lupine plant containing said homozygous recessive Tall gene that produces said dwarf plant height characteristic has been deposited under NCIMB No. 42442.

2. The lupine plant of claim 1, wherein said lupine plant is a tetraploid.

3. The lupine plant of claim 1, wherein said lupine plant is a diploid.

4. A lupine seed comprising said recessive Tall gene produced by growing the plant of claim 1.

5. A lupine plant, or a plant part thereof, produced by growing the seed of claim 4.

6. The plant part of claim 5, wherein the plant part comprises a cell, seed, protoplast, tissue culture, or vegetative cutting.

7. A tissue culture produced from protoplasts or cells from the plant of claim 1, wherein said cells or protoplasts are produced from a plant part selected from the group consisting of pollen, ovules, embryos, protoplasts, meristematic cells, callus, leaves, anthers, cotyledons, hypocotyl, pistils, roots, root tips, flowers, seeds, petiole, pods, and stems.

8. A lupine plant comprising said recessive Tall gene regenerated from the tissue culture of claim 7.

9. A method for producing lupine seed, said method comprising crossing two lupine plants and harvesting the resultant lupine seed, wherein at least one lupine plant is the lupine plant of claim 1.

10. A lupine plant, wherein the genome of said lupine plant is comprised of one or more species, and wherein said species is selected from *Lupinus polyphyllus, Lupinus arboreus, Lupinus sulphureus*, and *Lupinus nooktatensis*, and wherein said plant comprises a recessive Tall gene that when in a homozygous state, produces a dwarf plant height characteristic, wherein said dwarf plant height characteristic comprises a lupine plant having a plant height without raceme of less than 13.0 cm, wherein a representative sample of seed of said lupine plant containing said homozygous recessive Tall gene that produces said dwarf plant height characteristic has been deposited under NCIMB No. 42442.

11. The lupine plant of claim 10, wherein said lupine plant is a tetraploid.

12. The lupine plant of claim 10, wherein said lupine plant is a diploid.

13. A lupine seed comprising said recessive Tall gene produced by growing the plant of claim 10.

14. A lupine plant, or a plant part thereof, produced by growing the seed of claim 13.

15. The plant part of claim 14, wherein the plant part comprises a cell, seed, protoplast, tissue culture, or vegetative cutting.

16. A tissue culture produced from protoplasts or cells from the plant of claim 10, wherein said cells or protoplasts are produced from a plant part selected from the group consisting of pollen, ovules, embryos, protoplasts, meristematic cells, callus, leaves, anthers, cotyledons, hypocotyl, pistils, roots, root tips, flowers, seeds, petiole, pods, and stems.

17. A lupine plant comprising said recessive Tall gene regenerated from the tissue culture of claim 16.

18. A method for producing lupine seed, said method comprising crossing two lupine plants and harvesting the resultant lupine seed, wherein at least one lupine plant is the lupine plant of claim 10.

19. A lupine plant produced by growing a seed produced by the method of claim 9, wherein the genome of said plant comprises a recessive Tall gene that when in a homozygous state, exhibits a dwarf plant height characteristic comprising a plant height with raceme of less than 35.0 cm.

20. A lupine plant produced by growing a seed produced by the method of claim 18, wherein the genome of said plant comprises a recessive Tall gene that when in a homozygous state, exhibits a dwarf plant height characteristic comprising a plant height without raceme of less than 13.0 cm.

* * * * *